(12) United States Patent
Farley et al.

(10) Patent No.: US 6,638,273 B1
(45) Date of Patent: Oct. 28, 2003

(54) EXPANDABLE CATHETER HAVING IMPROVED ELECTRODE DESIGN, AND METHOD FOR APPLYING ENERGY

(75) Inventors: Brian E. Farley, Los Altos, CA (US); Grace Y. Schulz, San Carlos, CA (US); Dawn A. Henderson, Palo Alto, CA (US); Mark P. Parker, San Jose, CA (US); Arthur W. Zikorus, San Jose, CA (US); Gary H. Miller, Milpitas, CA (US); Jay S. Daulton, San Jose, CA (US); Douglas Portnow, Sunnyvale, CA (US)

(73) Assignee: VNUS Medical Technologies, Inc., San Jose, CA (US)

( * ) Notice: Subject to any disclaimer, the term of this patent is extended or adjusted under 35 U.S.C. 154(b) by 0 days.

(21) Appl. No.: 09/724,248

(22) Filed: Nov. 27, 2000

Related U.S. Application Data

(63) Continuation of application No. 08/895,850, filed on Jul. 17, 1997, now Pat. No. 6,152,899, and a continuation-in-part of application No. 08/717,994, filed on Sep. 26, 1996, now Pat. No. 6,033,397, and a continuation-in-part of application No. 08/720,209, filed on Sep. 26, 1996, now Pat. No. 6,139,527, which is a continuation-in-part of application No. 08/610,911, filed on Mar. 5, 1996, now Pat. No. 6,036,687.

(51) Int. Cl.[7] .............................................. A61B 18/04
(52) U.S. Cl. ........................................ 606/27; 606/32
(58) Field of Search ................................ 604/107, 104, 604/105, 106, 19–21, 93.01, 113; 607/96, 113, 124, 126, 1, 2, 101, 103, 122; 600/9, 11, 373, 372, 375; 606/27, 40, 32

(56) References Cited

U.S. PATENT DOCUMENTS 373,399 A    11/1887  Hamilton
659,409 A    10/1900  Mosher (List continued on next page.)

FOREIGN PATENT DOCUMENTS

DE    3516830    11/1986
EP    0 189 329    7/1986

(List continued on next page.)

OTHER PUBLICATIONS

O'Reilly, Kevin, *Endovenous Diathermy Sclerosis as a Unit of The Armamentarium for the Attack on Varicose Veins*; The Medical Journal of Australia, Jun. 1, 1974, p. 900.

(List continued on next page.)

*Primary Examiner*—Brian L. Casler
*Assistant Examiner*—Cris Rodriguez
(74) *Attorney, Agent, or Firm*—Fulwider Patton Lee & Utecht, LLP

(57) ABSTRACT

A catheter having expandable electrodes for applying energy to a hollow anatomical structure such as a vein. When used on a vein, the catheter is useful for a minimally invasive treatment of venous insufficiency. The catheter includes conductive end rings to which the electrodes are attached, for mechanically connecting and electrically tying electrodes together to provide for a single wire electrical connection points, for transmitting energy while more evenly spacing the electrodes. Expandable arms are formed of electrically conductive material and insulated along their length except for an intermediate section that functions as the electrode. The arms are tapered to allow more room for wiring and to reduce the possibility of shorting between the ends of the arms. The catheter further includes thermocouples in the electrodes for measuring temperatures on the outer surface of the electrode. Slots are formed in the arms for mounting the thermocouples. The temperature at the hollow anatomical structure is monitored and if a rapid, large temperature decrease of short duration is noted, the power is maintained constant as a fluid flush has been detected.

8 Claims, 8 Drawing Sheets

U.S. PATENT DOCUMENTS

| | | |
|---|---|---|
| 833,759 A | 10/1906 | Sourwine |
| 985,865 A | 3/1911 | Turner, Jr. |
| 3,230,957 A | 1/1966 | Seifert |
| 3,301,258 A | 1/1967 | Werner et al. |
| 3,557,794 A | 1/1971 | Van Patten |
| 3,920,021 A | 11/1975 | Hiltebrandt |
| 4,016,886 A | 4/1977 | Doss et al. |
| 4,043,338 A | 8/1977 | Homm et al. |
| 4,119,102 A | 10/1978 | LeVeen |
| 4,154,246 A | 5/1979 | LeVeen |
| 4,312,364 A | 1/1982 | Convert et al. |
| 4,346,715 A | 8/1982 | Gammell |
| 4,464,175 A | 8/1984 | Altman et al. |
| 4,512,338 A | 4/1985 | Balko et al. |
| 4,522,205 A | 6/1985 | Taylor et al. |
| 4,643,186 A | 2/1987 | Rosen et al. |
| 4,658,836 A | 4/1987 | Turner |
| 4,660,571 A | 4/1987 | Hess et al. |
| 4,664,120 A | 5/1987 | Hess |
| 4,699,147 A | 10/1987 | Chilson et al. |
| 4,709,698 A | 12/1987 | Johnston et al. |
| 4,765,331 A | 8/1988 | Petruzzi et al. |
| 4,776,349 A | 10/1988 | Nashef et al. |
| 4,807,620 A | 2/1989 | Strul et al. |
| 4,823,812 A | 4/1989 | Eshel et al. |
| 4,945,912 A | 8/1990 | Langberg |
| 4,966,597 A | 10/1990 | Cosman |
| 4,976,711 A | 12/1990 | Parins et al. |
| 4,979,948 A | 12/1990 | Geddes et al. |
| 5,010,894 A | 4/1991 | Edhag |
| 5,035,694 A | 7/1991 | Kasprzyk |
| 5,047,028 A | 9/1991 | Qian |
| 5,057,106 A | 10/1991 | Kasevich et al. |
| 5,057,107 A | 10/1991 | Parins et al. |
| 5,078,717 A | 1/1992 | Parins et al. |
| 5,098,429 A | 3/1992 | Stertzer |
| 5,098,431 A | 3/1992 | Rydell |
| 5,117,828 A | 6/1992 | Metzger et al. |
| 5,122,137 A | 6/1992 | Lennox |
| 5,156,151 A | 10/1992 | Imram |
| 5,188,602 A | 2/1993 | Nichols |
| 5,190,517 A | 3/1993 | Zieve et al. |
| 5,215,103 A | 6/1993 | Desai |
| 5,255,678 A | 10/1993 | Deslauriers et al. |
| 5,263,493 A | 11/1993 | Avitall |
| 5,275,610 A | 1/1994 | Eberbach |
| 5,281,218 A | 1/1994 | Imran |
| 5,293,869 A | 3/1994 | Edwards et al. |
| 5,314,466 A | 5/1994 | Stern et al. |
| 5,370,677 A | 12/1994 | Rudie et al. |
| 5,370,678 A | 12/1994 | Edwards et al. |
| 5,383,917 A | 1/1995 | Desai et al. |
| 5,397,339 A | 3/1995 | Desai |
| 5,403,312 A | 4/1995 | Yates et al. |
| 5,405,322 A | 4/1995 | Lennox et al. |
| 5,405,346 A | 4/1995 | Grundy et al. |
| 5,409,000 A | 4/1995 | Imram |
| 5,411,025 A | 5/1995 | Webster, Jr. |
| 5,419,767 A | 5/1995 | Eggers et al. |
| 5,423,815 A | 6/1995 | Fugo |
| 5,431,649 A | 7/1995 | Mulier et al. |
| 5,437,664 A | 8/1995 | Cohen et al. |
| 5,447,529 A | 9/1995 | Marchlinski et al. |
| 5,449,381 A | 9/1995 | Imran |
| 5,454,809 A | 10/1995 | Janssen |
| 5,458,596 A | 10/1995 | Lax et al. |
| 5,462,545 A | 10/1995 | Wang et al. |
| 5,465,717 A | 11/1995 | Imran et al. |
| 5,470,309 A | 11/1995 | Edwards et al. |
| 5,472,441 A | 12/1995 | Edwards et al. |
| 5,505,730 A | 4/1996 | Edwards |
| 5,514,130 A | 5/1996 | Baker |
| 5,545,161 A | 8/1996 | Imran |
| 5,556,396 A | 9/1996 | Cohen et al. |
| 5,582,609 A | 12/1996 | Swanson et al. |
| 5,626,578 A | 5/1997 | Tihon |
| 5,643,257 A | 7/1997 | Cohen et al. |
| 5,647,870 A | 7/1997 | Kordis et al. |
| 5,653,240 A | 8/1997 | Zimmon |
| 5,681,280 A | 10/1997 | Rusk et al. |
| 5,709,224 A | 1/1998 | Behl et al. |
| 5,735,280 A | 4/1998 | Sherman et al. |
| 5,810,804 A | 9/1998 | Gough et al. |
| 5,817,092 A | 10/1998 | Behl |
| 5,827,268 A | 10/1998 | Laufer |
| 5,836,947 A | 11/1998 | Fleischman et al. |
| 5,863,290 A | 1/1999 | Gough et al. |
| 5,868,740 A | 2/1999 | LeVeen et al. |
| 5,885,278 A * | 3/1999 | Fleischman ................. 600/374 |
| 6,014,579 A | 1/2000 | Pomeranz et al. |
| 6,014,589 A | 1/2000 | Farley et al. |

FOREIGN PATENT DOCUMENTS

| | | |
|---|---|---|
| EP | 0 205 851 | 12/1986 |
| EP | 0 472 368 A2 | 2/1992 |
| EP | 0 629 382 A1 | 12/1994 |
| EP | 0 738 501 A1 | 10/1996 |
| WO | WO 90/07303 | 7/1990 |
| WO | WO 92/12681 | 8/1992 |
| WO | WO 93/21846 | 11/1993 |
| WO | WO 94/07446 | 4/1994 |
| WO | WO 94/21170 | 9/1994 |
| WO | WO 95/02370 | 1/1995 |
| WO | WO 95/10236 | 4/1995 |
| WO | WO 95/10322 | 4/1995 |
| WO | WO 95/10978 | 4/1995 |
| WO | WO 95/31142 | 11/1995 |
| WO | WO 96/32885 | 10/1996 |
| WO | WO/97/06739 | 2/1997 |
| WO | WO 97/17892 | 5/1997 |
| WO | PCT/US98/14912 | 2/1998 |

OTHER PUBLICATIONS

Watts, G.T., *Endovenous Diathermy Destruction of Internal Saphenous*, Medical Journal, Oct. 7, 1972, p. 53.

O'Reilly, Kevin, *Endovenous Diathermy Sclerosis of Varicose Veins*, The Australian, New Zealand Journal of Surgery, vol. 47, No. 3, Jun. 1977, p. 393.

O'Reilly, Kevin, *A Technique of Diathermy Sclerosis of Varicose Veins*, The Australian, New Zealand Journal of Surgery, vol. 51, No. 4, Aug. 1981, p. 379.

Cragg et al., *Endovascular Diathermic Vessel Occlusion*, Diagnostic Radiology, 144: 303–308, Jul. 1982.

Ogawa et al., *Electrothrombosis as a Treatment of Cirsoid Angioma in the Face and Scalp and Varicosis of the Leg*, Technical Notes, No. 3, Oct. _, p. 310, 19_.

Brunelle, et al., *A Bipolar Electrode for Vascular Electrocoagulation with Alternating Current*, Technical Notes, Oct. _, p. 239.

, *Electrogulguration for Varicose Veins*, the Medical Letter on Drugs and Therapeutics, Jul. 12, 1968, p. 54.

* cited by examiner

EXPANDABLE CATHETER HAVING IMPROVED ELECTRODE DESIGN, AND METHOD FOR APPLYING ENERGY

This application is a continuation of application Ser. No. 08/895,850 filed Jul. 17, 1997, now U.S. Pat. No. 6,152,899 which is Continuation-in-part of application Ser. No. 08/610,911 filed Mar. 5, 1996, now U.S. Pat. No. 6,036,687 and a Continuation-in part of application Ser. No. 08/717,994 filed on Sep. 26, 1996, now U.S. Pat. No. 6,033,397 and a Continuation-in-part of application Ser. No. 08/720,209 filed Sep. 26, 1996, now U.S. Pat. No. 6,139,527.

BACKGROUND

The invention relates generally to catheters and more particularly, to expandable catheters having electrodes for applying energy to biological tissue, and methods therefor.

The venous system contains a plurality of valves for directing blood flow back to the heart. The venous system of the lower limb consists essentially of the superficial venous system and the deep venous system with perforating veins connecting the two systems. The superficial system includes the great saphenous vein and the small saphenous vein. The deep venous system includes the anterior and posterior tibial veins which unite to form the popliteal vein which in turn becomes the femoral vein when joined by the small saphenous vein.

In FIG. 1 there is shown a partial cross-sectional view of a dilated vein 10 from a lower limb having competent valves 12. Venous valves are usually bicuspid valves, with each cusp forming a sack or reservoir 16 for blood which, under pressure, forces the free edges of the cusps together to prevent retrograde flow of the blood and allow only antegrade flow to the deep veins and heart. The arrow 18 leading out the top of the vein represents the antegrade flow of blood back to the heart. Properly operating venous valves prevent retrograde flow as blood is pushed forward through the vein lumen and back to the heart. When an incompetent valve 14 attempts to close in response to a pressure gradient across the valve, the cusps do not seal properly and retrograde flow of blood occurs. Venous insufficiency is a chronic disease involving the incompetence of venous valves.

Chronic venous insufficiency is a problem caused by hydrodynamic forces acting on the lowest part of the body: the legs, ankles and feet. As the veins dilate due to increased pressure, the retrograde flow of blood may occur and the valves in the veins become less able to withstand the weight of the blood above them. The weight of the blood causes the veins to dilate further and the valves in the veins to fail. Localized incompetence of a valve in a perforator vein allows reflux of blood from the deep venous system to the superficial venous system. Reflux may be expressed as the peak reverse velocity of blood as a function of vein diameter. Patients with phlebitis may have damaged vein valve leaflets.

Patients who develop chronic venous insufficiency of the lower extremities frequently develop complications of this disease, including skin discoloration, varicose veins, and ulcerations. These patients may develop blood clots in their legs which can travel to their lungs, resulting in a pulmonary embolism. These complications develop over time, with increasingly severe damage to the veins and the valves within the veins.

The varicose vein condition includes dilation and tortuosity of the superficial veins of the lower limbs, resulting in unsightly discoloration, pain, swelling, and possibly ulceration. Varicose veins often involve incompetence of one or more venous valves, which allow reflux of blood within the superficial system. This can also be worsened by deep venous reflux and perforator reflux. Current treatments include surgical procedures such as vein stripping, ligation, and occasionally, vein segment transplant, venous valvuloplasty, and the implantation of various prosthetic devices. The removal of varicose veins from the body can be a tedious, time-consuming procedure having a painful and slow healing process. In addition, patients with varicose veins may undergo injection sclerotherapy, or removal of vein segments. Complications, scarring, and the loss of the vein for future cardiac and other by-pass procedures may also result. Along with the complications and risks of invasive surgery, varicose veins may persist or recur, particularly when the valvular problem is not corrected. Due to the long, technically demanding nature of the surgical valve reconstruction procedure, treating multiple venous sections with surgical venous valve repair is rarely performed. Thus, a complete treatment of all important incompetent valves has been impractical.

Venous insufficiency often consists of hypertension of the lower limb in the deep, perforating and often superficial veins. Existing treatments for chronic venous insufficiency are often less than ideal. These treatments include the elevation of the legs, compressing the veins externally with elastic support hose, perforator ligation, surgical valve repair, and grafting vein sections with healthy valves from the arm into the leg. These methods have variable effectiveness. Moreover, invasive surgery has its associated complications with risk to life and expense. Similarly, the palliative therapies require major lifestyle changes for the patient. For example, the ulcers may recur unless the patient continues to elevate the legs and use pressure gradient stockings for long continuous periods of time.

Due to the time-consuming and invasive nature of the current surgical treatments, such as valvuloplasty or vein segment grafting, typically only one valve is treated during any single procedure. This greatly limits the ability of the physician to fully treat patients suffering from chronic venous insufficiency. Every instance of invasive surgery, however, has its associated complications with morbidity and expense.

Another type of treatment, the ligation of vascular lumina by cauterization or coagulation using electrical energy from an electrode, has been employed as an alternative to the surgical removal of superficial and perforator veins. However, such ligation procedures also close off the lumen, essentially destroying its functional capability. For example, it is known to introduce an electrode into the leg of a patient, and position the electrode adjacent the exterior of the varicose vein to be treated. Through a small stab incision, a probe is forced through the subcutaneous layer between the fascia and the skin, and then to the vein to be destroyed. A monopolar electrode at the outer end of the probe is placed adjacent the varicose vein and the return electrode is placed on the skin. Once properly positioned, an alternating current of 500 kHz is applied to destroy the adjacent varicose vein by electrocoagulation. The coagulated vein loses the function of allowing blood to flow through, and is no longer of use. For example, occluding or ligating the saphenous vein would render that vein unavailable for harvesting in other surgical procedures such as coronary by-pass operations.

Catheters having bowable or expandable arms with electrodes mounted on the arms may be used to apply energy to the inside surface of a hollow anatomical structure. In shrinking a vein for instance, it is desirable to apply energy evenly around the entire inner surface of the vein at the treatment location so that the full inner surface is evenly heated. The evenly-heated surface should then contract more uniformly to shrink the vein diameter. To apply energy to the vein wall, it is preferable to bring a plurality of evenly-spaced electrodes into apposition with the vein tissue. It is also preferable to use electrodes that are as wide as possible as the wider sized electrodes will be closer together when in apposition with the vein wall and will result in a more even application of energy to the vein wall.

However, having large electrodes on small catheters can increase the chances of shorting between those electrodes in which case no power will be applied to the target tissue. Bowable arms that have been made larger to support larger electrodes will allow less room at the anchor points of the arms to the catheter body causing them to be closer together which also provides less room for wiring the electrodes in the arms. Wiring is not only needed for energizing the electrodes on the bowable arms, but may also be needed for a temperature sensor mounted on an electrode or electrodes. Reducing the number of wires can greatly alleviate this concern.

Further considerations in the design of a reliable and effective bowable catheter for applying energy to a hollow anatomical structure include the control over forces that may be asymmetrical and that may tend to cause the arms to expand and contract so that they are not uniformly spaced. Additionally, improvements in the mounting of temperature sensors to the bowable arms may also increase effectiveness of the catheter.

Yet another consideration in the design of expandable catheters is the ability to provide a fluid flush or other useful fluid from the catheter or through a coaxial vascular sheath into the biological structure in which the catheter is used. Such fluids may be used to clear the biological structure of undesirable fluids, or to provide a radio-opaque fluid for a catheter location process, or for delivering therapeutic drugs, or for other reasons. However, applying a fluid from the catheter or a coaxial sheath to the biological structure may have the effect of lowering the temperature at the electrode or electrodes. Should that electrode or electrodes have a temperature sensor, the power control system connected to the catheter may mistakenly apply additional power to the electrode to increase the temperature of the biological structure, only to find that when the fluid flush is terminated, the temperature is now too high. The power control system must then terminate the application of power to the electrode on the arm. It would be desirable to avoid this form of power cycling when a fluid flush is applied by the catheter operator.

A consideration applicable to expandable catheters is the avoidance of fluid leakage into the catheter around movable parts. Another consideration is the avoidance of catheter distortion through use of those movable parts. For example, operating the expansion mechanism to control the expansion and contraction of the expandable arms may subject the catheter shaft to axial stresses that tend to undesirably lengthen or compress the catheter shaft. At the same time, it is desirable to maintain catheter shaft flexibility.

Hence, those skilled in the art have recognized the needs for an expandable electrode catheter that has increased electrode size while maintaining the catheter size as small as practical, in addition to providing improved control over forces that may tend to adversely affect the operation of the expandable arms as well as the catheter shaft. Additionally, those skilled in the art have recognized the need for an improved mounting technique for temperature sensors to the expandable arms as well as the avoidance of fluid leakage into the catheter around movable parts, while maintaining catheter shaft flexibility. Recognized also is the need for control over the power system coupled to the catheter so that unnecessary cycling does not occur when fluid flushes have been applied by the catheter operator. The invention fulfills these needs as well as others.

SUMMARY OF THE INVENTION

Briefly, and in general terms, the present invention provides a minimally invasive apparatus and method for solving the underlying problems of venous insufficiency and uses a novel repair system, including an energy delivery catheter for applying energy to a selected tissue site. Additionally, the present invention is useful for shrinking other hollow anatomical structures.

Features of the present invention include providing a bowable electrode catheter to apply energy to a selected hollow anatomical structure. In the case of a venous treatment site, the bowable electrode catheter applies energy to restore the competence of venous valves, normalize flow patterns, dynamics, and pressure; reduce sections of dilated varicose veins to a normal diameter for cosmetic purposes, and treat veins such that they remain patent in that their valves can resume their function and return blood to the heart.

One feature of the present invention is to provide such an apparatus for applying energy to cause shrinkage of a hollow anatomical structure, comprising a catheter having a shaft, an outer diameter and a working end, wherein the outer diameter of the catheter is less than the inner diameter of the hollow anatomical structure. A plurality of electrodes are located at the working end, two of which are connected together at a common electrically conductive device, for single point wire attachment. The plurality of electrodes produce an energy field to heat a treatment area adjacent the electrodes to cause preferential shrinkage of the hollow anatomical structure.

Other features of the present invention include ring members for mechanically and electrically interconnecting electrodes to provide single wire contacts for transmitting energy while obtaining precise, even spacing between the electrodes. Additionally, electrodes are mounted on tapered arms, the tapers allowing more room between the arms at their mounting points to the catheter body. At the same time, mounting the arms to the catheter body is made easier.

Another feature of the present invention is a temperature sensor for measuring temperatures at the electrode. In a more detailed aspect, an opening is formed in the electrode to receive the sensor, the opening having an oval or slot shape so that there remains sufficient electrode material between the sensor and the side of the electrode to retain electrode mechanical strength. This feature reduces the possibility of electrode fracture due to repeated expansion and contraction and increases the attachment strength of the sensor to the electrode. The opening is adapted to result in more reliable sensor potting and a less bulky profile. In yet a further aspect, the sensor wires are located on either side of the electrode.

An additional aspect of the present invention is a tension wire located in the catheter shaft to prevent elongation of the catheter during electrode expansion.

A further feature of the present invention is to provide an outer tube having a spring coil enclosed in a polymer to form the outer shaft of the catheter for reducing axial compressibility while increasing flexibility.

Another feature of the present invention is to provide means for automatically detecting a fluid flush, sensing temperature changes resulting therefrom, and controlling the application of power to avoid undesired cycling.

Yet a further aspect of the present invention is to apply an external pressure exerting device to the treatment area sufficient to compress the hollow anatomical structure to the desired diameter before the application of energy.

The present invention further includes a method of applying energy to cause shrinkage of a hollow anatomical structure, the method comprising the steps of introducing a catheter having a working end with bowable electrodes for applying energy to the hollow anatomical structure. The method also includes the step of mechanically and electrically interconnecting the electrodes to result in fewer wires and greater precision in spacing the electrodes from one another.

These and other aspects, features, and advantages of the present invention will become apparent from the following more detailed description, when taken in conjunction with the accompanying drawings which illustrate, by way of example, the preferred embodiments of the invention.

DETAILED DESCRIPTION OF THE PREFERRED EMBODIMENTS

Figure 2:
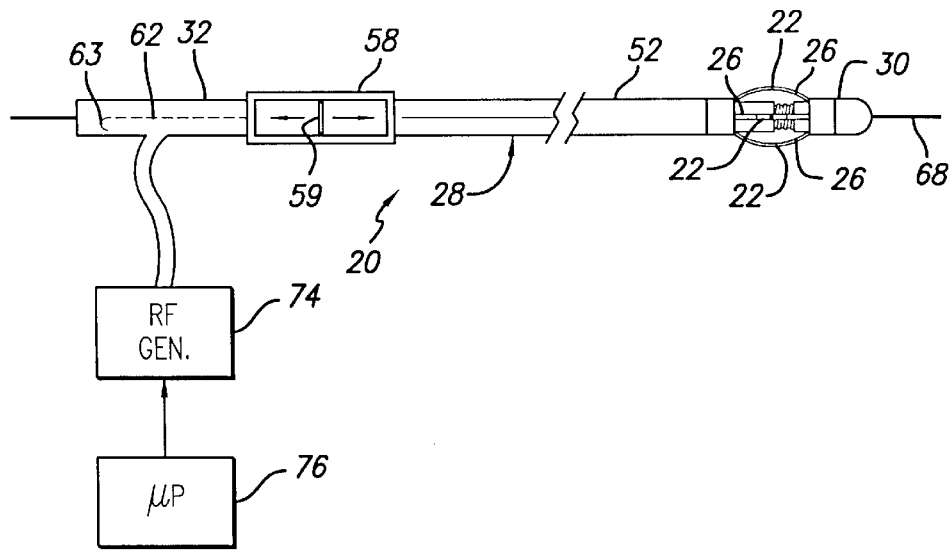
FIG. 2 is a diagram of an RF energy system with a catheter having expandable electrodes for imparting energy to treat a vein.
Figure 3:
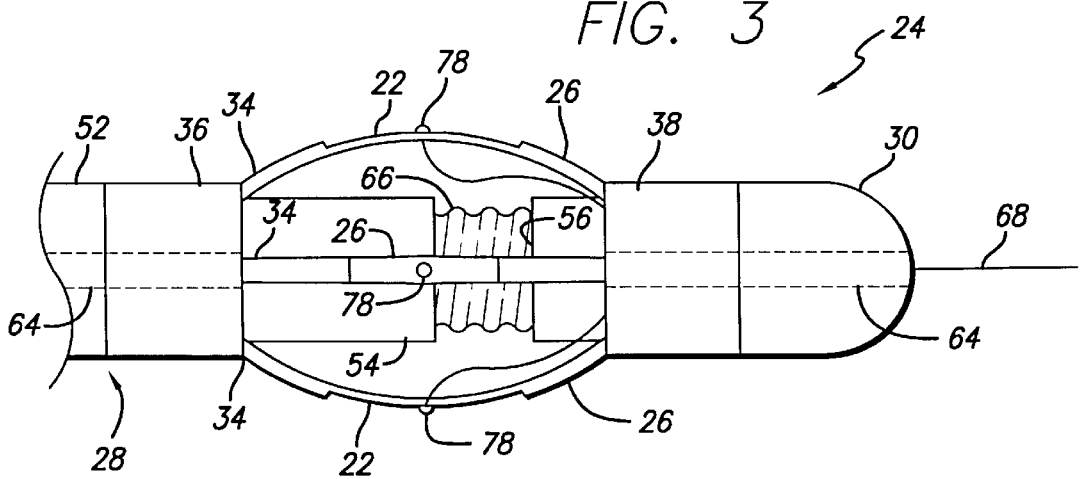
FIG. 3 is an enlarged side view of the working end of the embodiment of the catheter shown in FIG. 2 showing the expandable arms and electrodes in an expanded position, temperature sensors, guide wire, and stop surface arrangement, in accordance with aspects of the present invention.

Referring now to the drawings in which like reference numerals are used to refer to like or corresponding elements among the several views, there is shown in FIGS. 2 and 3, an apparatus for minimally invasive treatment of venous insufficiency and valvular incompetency that includes a catheter 20 for delivering electrodes 22 to a venous treatment site. The catheter 20 further includes a working end 24, which includes electrodes 22 on expandable arms 26, a shaft 28, a working end tip 30, and a handle or connecting end 32. In the embodiment of FIGS. 2 and 3, the catheter 20 includes four conductive arms 26 although only three can be seen. The arms 26 can be expanded or bent or bowed outward as shown. The arms 26 are formed of an electrically conductive material such as stainless steel, spring steel, or a shape memory material such as that commonly referred to as Nitinol™. To restrict energy transmission to the desired portion of the arm 26, i.e., to the electrode 22, the arms 26 are surrounded by insulation, except for the exposed conductive surface area that serves as the electrode. The electrode 22 of the arm 26 may be formed by cutting the insulation layer away with a laser or by other means.

The insulation on the arms 26 may comprise parylene applied by vapor deposition, PET that is shrunk over the arms or coated on the arms, polyimide that is shrunk over the arms, polyurethane that is coated on the arms, or another type of application process or insulating material that may be deposited in a vacuum chamber, extruded, heat shrunk, or otherwise applied onto the arms 26. The insulation is also provided along the inner surfaces of the expandable arms 26 away from the electrodes 22 and further covers the peripheral edges of the exposed face of the electrode 22 to prevent heating the blood flowing in the vein and reduce the likelihood of coagulation.

Unless otherwise noted, the term "working end" will refer to the direction toward the treatment site in the patient, and the term "connecting end" will refer to the direction away from the treatment site in the patient. The following embodiments are directed to the treatment of the venous system of the lower limbs. It is to be understood, however, that the invention is not limited thereto and can be employed intraluminally to treat other biological structures, as is discussed below.

Figure 4:
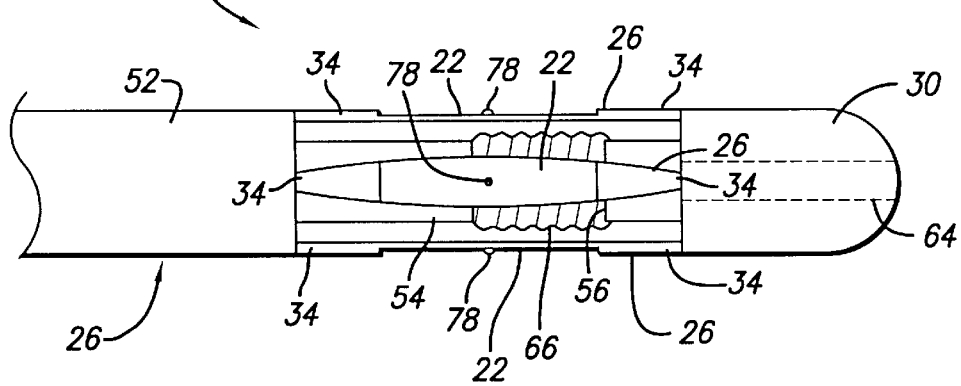
FIG. 4 is a view similar to FIG. 3 showing the expandable arms and electrodes in a contracted position.

The expandable arms 26 may be fabricated so that they are biased to return to the reduced diameter profile shown in FIG. 4. The use of metal arms 26 results in such biasing. The arms may have a thickness ranging from 0.13 mm to 1.27 mm and preferably between 0.38 mm and 0.76 mm, to allow four or more electrodes around the catheter shaft. Rounded wires may also be used with a diameter preferably between about 0.13 mm to 0.38 mm, but can be up to about 0.76 mm.

The expandable arms 26 are preferably tapered at each end 34, such that there is a larger electrode surface area 22 located at the midpoint between the two ends 34. The smaller ends 34 reduce the possibility of contact with the ends of other arms at their mounting points in the catheter and leave more room for wiring temperature sensors mounted to the arms, as is described below in greater detail. For example, the center width of the arms 26 in the embodiment shown is 0.76 mm with the arms symmetrically tapering to a width of 0.38 mm at both ends 34. The lengths of the arms 26 range from 30.5 mm to 32.5 mm, and the thickness ranges from 0.10 to 0.12 mm.

Figure 5A:
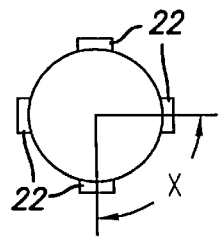
FIGS. 5A and 5B present schematic views of the distances between electrodes in the contracted position of FIG. 4 and in the expanded position of FIG. 3.
Figure 5B:
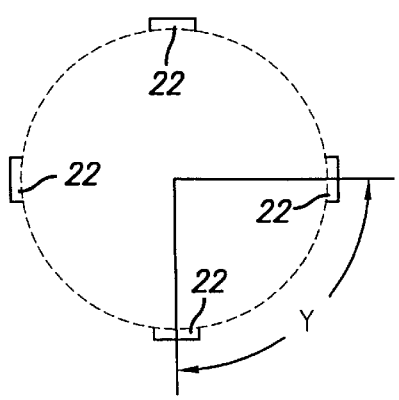

Referring to FIGS. 5A and 5B, it can be seen that the spacing between the electrodes 22 increases during expansion. FIG. 5A presents a schematic of the positions of the electrodes when the expandable arms are in their contracted configuration, and demonstrates the spacing "X" between the electrodes 22. The spacing between the electrodes 22 increases to the much greater spacing "Y" as seen in FIG. 5B, which is also a schematic view that shows the positions of the electrodes when the arms are in their expanded positions. As is known to those skilled in the art, the current and power densities decrease as the distance between electrodes increases and thus, the current and power densities along the "Y" distance are less than along the "X" distance. However, using tapered arms in accordance with the embodiment described above wherein the electrodes are located at the greatest width of the arms will result in those electrodes being closer together by that width. This results in increased current and power densities.

Figure 6:
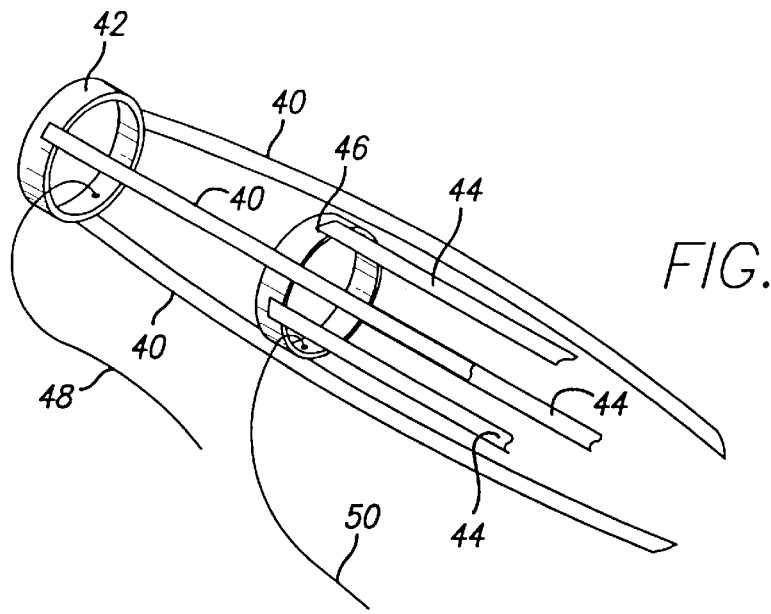
FIG. 6 is an enlarged perspective view of an embodiment of expandable arms with common ring connectors in accordance with an aspect of the present invention.
Figure 6A:
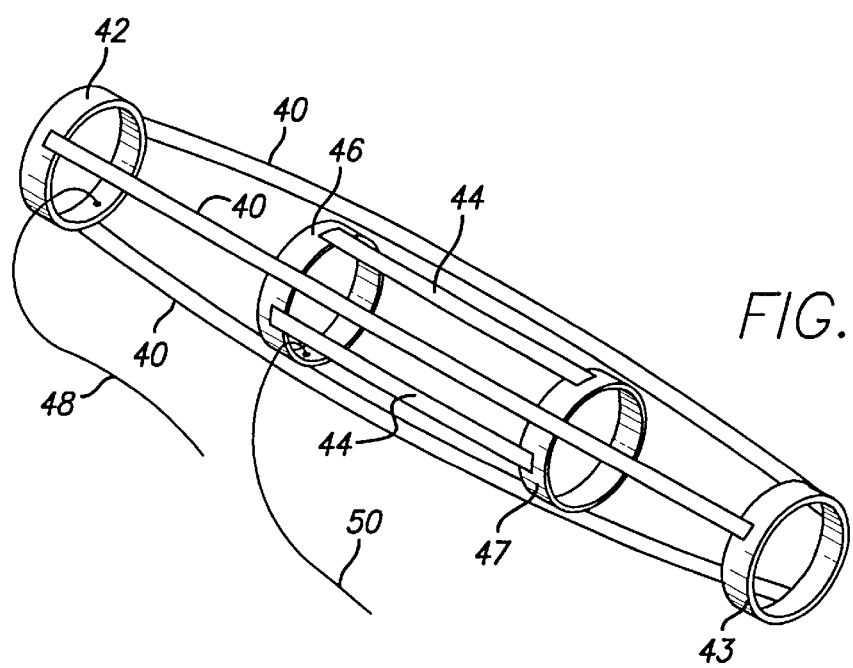

Turning now to FIG. 6, a configuration used to reduce the number of wires and the wiring complexity in the working end 24 of the catheter (FIGS. 2 and 3) as well as make placement of the arms 26 more even and increase manufacturing ease is shown. Sets of expandable arms are commonly attached, or formed, on a connecting strip or ring. The connecting ring is electrically conductive as are the arms and therefore, only one electrical attachment is necessary to each set of arms. In particular, a first set of three expandable arms 40 is attached to a first common connecting ring 42. A second set of three expandable arms 44 is attached to a second common connecting ring 46. Both sets of arms have their respective expandable arms spaced equidistantly from one another at 120°. The second set of arms is rotated relative to the first set so that there is 60° between adjacent arms in the combined sets of arms. The first and second sets of expandable arms 40 and 44 each consists of half of the total number thereof.

The first and second rings each have a single electrical conductor 48 and 50 respectively attached to the inside surfaces to provide power to the ring and the associated arms, with their electrodes. In a bipolar application, one conductor would be connected to the positive polarity and the other connected to the negative polarity. The electrode rings have, for example, a 1.5 mm inside diameter and a 1.6 mm outside diameter, and are 1.0 mm thick. In one embodiment, they are formed of silver-plated stainless steel.

In one embodiment, the first ring 42 and second ring 46 have their arms attached to the outside of their respective rings. While the arms of one may touch the ring of the other, electrical contact is avoided due to the insulation on the arms. The arms overlap the rings by approximately 0.5 mm and are held in place.

The connection of the arms 40 and 44 to the rings 42 and 46 may be accomplished by spot welding or alternatively may be accomplished by soldering or through the use of an electrically conductive adhesive. Such a connection may also be made by forming the ring of one continuous strip or piece of material, where the arms are tabs on the strip that may be bent down into place from a central disk or they may be formed by other means. The other, non-interconnected ends of the arms are, in this embodiment, held in place on a catheter shaft by adhesive, such as epoxy. A sleeve is then placed over these ends of the arms in tight contact with the arm ends and the epoxy. This is described in further detail below.

The use of the common connector rings 42 and 46 results in less wiring through the catheter shaft 28 and at the working end tip 30 of the catheter allowing the catheter to be made smaller. Fewer connections and parts result in increased reliability as well. Manufacturing is made easier as the placement of the arms in relation to each other is accomplished outside the catheter. Greater precision in the spacing of the arms is possible as well as ease in manufacturing because the catheter need not be handled as the arms are welded into position. The greater precision in the spacing of the arms resulting from the use of the connector rings 42 and 46 will result in a more even application of energy to the wall of the hollow anatomical structure and a more even heating of that wall. More uniform current and power densities will be applied.

Although shown as sets of three arms, different numbers of arms may be used. For example only two arms may be connected to a common connection ring, or a greater number, such as four. Typically, hollow anatomical structures with larger inner diameters are treated with a greater number of arms. The use of the ring with only two arms nevertheless results in less wiring at the working end of the catheter because each arm need not be wired separately. Alternatively, the arms need not be equidistantly spaced about their respective rings. They may all be located on one side of a diametrical line for example, while a second ring has another set of arms located on the opposite side of the diametrical line. When the first and second rings are combined however, the arms would be equally spaced about the periphery. The use of insulation (e.g. parylene) on the arms prevents electrical short circuits.

The rings 42 and 46 are mounted in the catheter at the working end tip 30 in this embodiment with the non-interconnected ends of the arms pointing towards the connecting end. Other arrangements are possible however. For example, both ends of the arms may be connected to interconnecting rings. Such an arrangement would provide even greater control over the spacing of the arms in that both ends of each arm would be precisely located and spaced from the other arms. This arrangement would result in even greater precision of that spacing. In another arrangement, the arms may be mounted to interconnecting rings that are located at the connecting end side of the working end. The non-interconnected ends of the arms would, in this case, be pointing towards the working end tip 30. Instead of connecting a wire to the ring in this case, the electrical wire may be connected to an arm at the working end tip and because of the interconnecting ring providing an electrical path among its respective arms, all interconnected arms will be of the same polarity. However, the electrical wires may be connected to the arms in accordance with other schemes.

Returning again to FIGS. 2, 3, and 4, the expandable arms 26 are connected at their ends on the connecting end side of the working end to a slidable outer shaft or tube 52 under a connecting sleeve 36 and at their opposite ends to the rings 42 and 46 that are fixedly mounted in the working end tip 30 under a tip sleeve 38. The sleeves 36 and 38 can be fabricated from polyimide. The sleeve 38 not only provides a smooth transition from the outer shaft to the arms and vice versa, but also provides a redundant attachment of the arms to the catheter. As described above, the ends of the arms are attached to the catheter shaft by epoxy. The sleeve 38 is tightly mounted over the arm ends and epoxy to also hold the arms to the shaft. The slidable outer tube controls the extent of the expansion of the arms 26 for proper treatment of vein lumina having different inner diameters. An inner stop tube 54 is connected to the slidable tube 52 and moves with it, acting as a stop device by making contact with a stop surface 56 that is fixed in position to the working end tip 30. The inner stop tube 54 thus interacts with the stop surface 56 to limit the amount of expansion of the expandable arms 26.

Referring now to FIG. 4, the slidable tube 52 extends to the connecting end 32 and the arms 26 are in their contracted or collapsed positions. As the tube 52 is slid in the direction of the working end 24, it causes the ends 34 of the expandable arms 26 to move closer together thus causing the center section of the arms, with their electrodes 22, to expand outwardly from the catheter shaft, as shown in FIGS. 2 and 3, to make contact with the vein wall. Thus, as the outer slidable tube 52 is moved towards and away from the working end 24 of the catheter in response to movement at a control actuator 58 located at the connecting end 32 of the catheter, the electrodes 22 are urged radially outward and inward, respectively. The working end tip 30 essentially remains stationary while the outer slidable tube 52 is moved. The outer slidable tube 52 may be moved a preset distance to cause the arms 26 to bow outwardly to a known diameter. Such known diameter or diameters may be indicated by gradients or other indicia placed on the actuator 58. By manipulating the slidable outer tube 52 to adjust the effective diameter of the electrodes 22, contact between the electrodes 22 and the venous tissue can be established and subsequently maintained during shrinkage.

The control actuator 58 may take the form of a sliding switch 59, a lever, a threaded control knob, or other suitable mechanism, preferably one that can provide fine control over the movement of slidable outer tube 52. By using the control actuator 58 to move the tube 52, the effective diameter of the electrodes 22 can be closely controlled for treating vein lumina to provide varying degrees of vein shrinkage and precise control of the final desired diameter. The outer tube 52 is preferably designed to minimize axial compressibility of the tube 52 in order to reduce the necessity for large movements by the actuator 58, and to prevent the undesired collapse of the expandable arms 26.

The slidable outer tube 52 in one embodiment is made thicker to have increased column strength. In one case, its thickness was 0.05 mm. At this thickness, the axial compressibility of the tube 52 is reduced, lessening the need for a large lever or switch 59 motion at the handle, and preventing the arms 26 from collapsing. In another arrangement, the slidable outer tube 52 is made of a different material having a greater column strength, for example polyimide instead of polyethylene, and may or may not be thicker. In another embodiment, the slidable outer tube 52 may be formed of two or more coaxial tubes bonded together at their ends to form a thickened tube.

Figure 7:
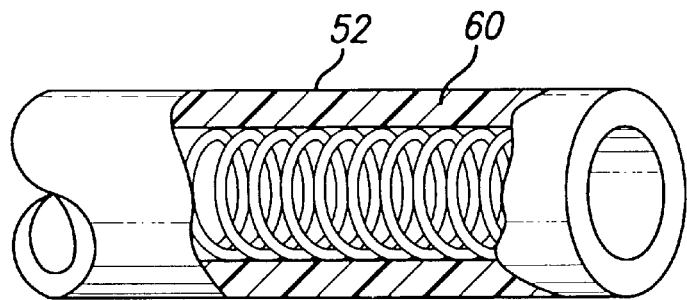
FIG. 7 is a partially cut-away perspective view of a tube having an enclosed coiled spring.

In yet another embodiment, the slidable outer tube 52 may comprise an enclosed spring 60, as shown in FIG. 7 to reduce axial compressibility, provide more column strength when pulled and pushed, and yet allow for shaft flexibility. The polymer material that encloses the spring in the outer tube 52 may comprise PET or polyethylene. The spring 60 may be formed of stainless steel or other material.

The sleeve 36 at the connecting end side of the working end provides a smooth transition from the slidable tube 52 over the ends 34 of the expandable arms 26. In one embodiment, the sleeve 36 comprises a tapered portion to transition from the diameter of the slidable tube 52 to the arms 26. In a second embodiment, polyimide or preferably a softer material such as silicone would serve as an intermediate step or diameter between the slidable tube 52 and the sleeve 36. If using a shrink tubing to form the transition, a PET is preferred because of its thin wall. Rather than heat shrunk, adhesive may be used to provide a smooth transition.

Figure 8:
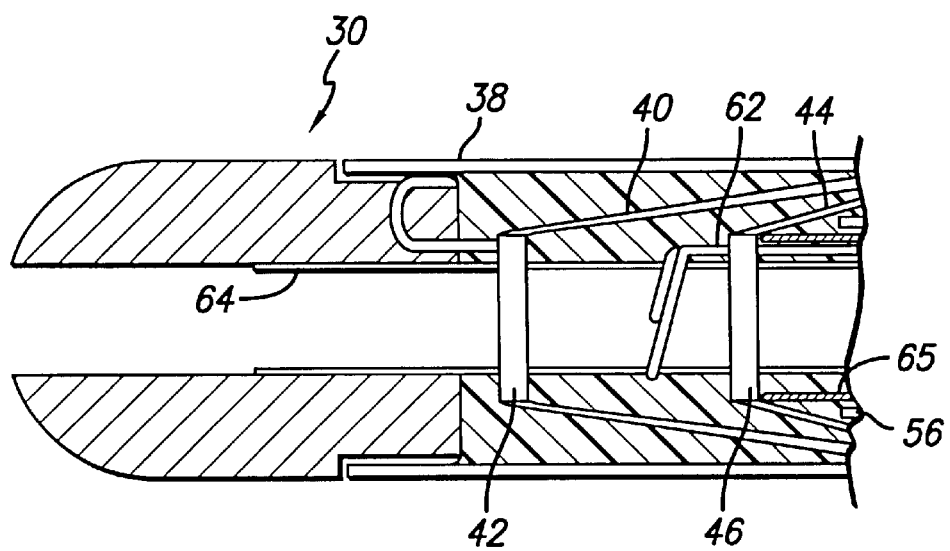
FIG. 8 is an enlarged cross-section view of a tension wire embedded in the working end tip of the catheter shaft in accordance with an aspect of the present invention.

Pushing the outer tube 52 over the inner shaft of the catheter in the working end direction against the bias of the expandable arms 26 that are anchored to the working end tip 30 applies axial force against the inner catheter shaft that may tend to elongate or stretch the inner shaft. To avoid possible stretching of the catheter shaft, a metal tension wire 62, as shown in FIG. 8, runs along the length of the inner shaft assembly and is anchored at each end to prevent elongation of the inner tube during expansion of the arms 26. The tension wire 62 and its termination at the connecting end and working end are partially shown in dashed lines in FIG. 2. At the connecting end of the catheter 20, the tension wire 62 is terminated in a hook shape 63. At the working end, the tension wire 62 is wrapped around the lumen 64 twice between the two interconnecting rings 42 and 46. The tension wire is fully encapsulated or "potted" in adhesive fixing it to the catheter shaft. In one embodiment, the wire 62 was formed of stainless steel having a diameter of 0.25 mm. Materials other than stainless steel may be used for the tension wire 62 such as tungsten or other metals.

As shown in FIG. 8, the tension wire 62 is placed in an off-center position to allow room for an axially-located lumen 64 that may be used for a guide wire or for conducting fluids. In FIG. 8, the end of the tension wire is shown wrapped around the lumen 64 at a position between the interconnecting rings 42 and 46 in the distal tip side of the working end. The tension wire 62 may also be terminated in various other ways such as ending straight or soldered to a ring or washer before being potted into adhesive. Wires extended to the working end of the catheter from the connecting end may be wound around the tension wire 62, or the lumen 64, or both.

The lumen 64 can include a separate tubing having sufficient length to traverse the length of the catheter. As shown in FIG. 8, the tubing for the 64 lumen ends just after the tip sleeve 38 so that the remainder of the tip 30 can remain flexible. The tubing for the lumen 64 can be fabricated from polyethylene. At the working end of the catheter, the lumen 64 is surrounded by the two interconnecting rings 42 and 46, and the tension wire 62. The end of the tension wire is wrapped around the tubing of the lumen 64. The lead wires (not shown) for the electrical connections and thermocouple can be set alongside the lumen 64. A secondary sleeve 65 surrounding a portion of the lumen ends at the second ring 46. The tension wire 62 and the lead wires are sandwiched between secondary sleeve 65 and the lumen 64. The stop sleeve 56 is located between the secondary sleeve 65 and the tip sleeve 38. Epoxy fills the space between the lumen 64 and the tip sleeve 38, and the rings 42 and 46 and the tension wire 62 are fixed or potted into position. The sets of expandable arms 40 and 44 exit the epoxy-filled sleeve to form the arms 26 of the electrode catheter. The flexible portion of the tip 30 can be attached to the sleeve by an adhesive such as cyanoacrylate. A hook projecting from under the base of the first ring 42 can engage the flexible portion of the tip to act as a secondary attachment and further secure the flexible portion in place. The hook can be encapsulated under the ring 42 by adhesive or epoxy.

The clearance between the outer tube 52 over the inner shaft necessary for sliding movement produces the possibility of undesired fluid leakage into the catheter between the moving parts. Referring again now to FIGS. 2, 3, and 4, a fluid sheath 66 preferably taking the form of a bellows prevents fluids from entering the catheter. The bellows 66 may comprise a plastic tube with its ends secured onto the working end of the inner stop tube 54 and to the stop surface 56, thereby preventing fluid from getting between the moving parts. The bellows 66 folds up when sliding motion of the outer tube 52 over the inner shaft expands the expandable arms 26. The bellows 66 may be blown in a mold or free-blown for initial expansion, and may be heat shrunk, press fit, or adhered with adhesive to its mounting surfaces to form a fluid-tight seal. A bellows 66 is particularly useful in that it permits unrestricted movement of the slidable outer tube 52 yet seals the sliding parts from fluid leakage.

Referring again to the lumen 64 shown in FIGS. 3, 4, and 8, the lumen 64 has a size large enough to accept a guide wire 68 (FIG. 3). The lumen 64 through which the guide wire 68 passes is preferably insulated so as to prevent or minimize any coupling effect the electrodes 22 may have on the guide wire 68. If desired, the guide wire 68 can be removed before the application of RF energy to the electrodes 22 to allow the guide wire lumen 64 to be used for the delivery or perfusion of medicant and cooling solution to the treatment area during the application of the RF energy.

The working end tip 30 can include a flexible nosecone shape, but can have other atraumatic shapes that facilitate tracking of the catheter 20 over the guide wire 68 and through bends in the venous vascular system of the patient. The nosecone-shaped tip 30 can be fabricated from a flexible polymer having a soft durometer, such as 44 Shore A. Alternatively, the working end tip 30 can be constructed from a spring covered with a thin layer of polyethylene shrink tubing.

Referring once again to FIG. 2, a system in accordance with aspects of the invention is shown. The electrodes 22 on the bowable arms 26 are connected to an RF generator 74 controlled by a processor 76 which in this case, is a microprocessor located within the generator 74. The processor 76 controls the RF generator 74 to apply energy to the electrodes 22 to generate heat in the target tissue. Depending on the processor, both the length of time that energy is applied and the level of that energy may be programmed. In addition, the embodiment of FIG. 3 also includes a temperature sensor 78 mounted on each arm 26, in the electrode area 22 in this case. FIG. 3 is not drawn to scale and the actual temperature sensor may be much smaller than that shown, such as that shown in FIG. 4, or smaller. Signals from the temperature sensors 78 are coupled to the microprocessor 76 which compares them to a threshold temperature or temperatures to determine if RF energy to the electrodes 22 should be interrupted or should be continued. The microprocessor 76 controls the RF generator 74 accordingly. Although shown as going through the RF generator 74 in FIG. 2, the signals from the temperature sensors 78 may be provided directly to the microprocessor 76 in a different embodiment. Temperature feedback permits control over the application of power to heat and thereby shrink the collagen effectively, as described below, without damaging surrounding tissue.

Figure 9:
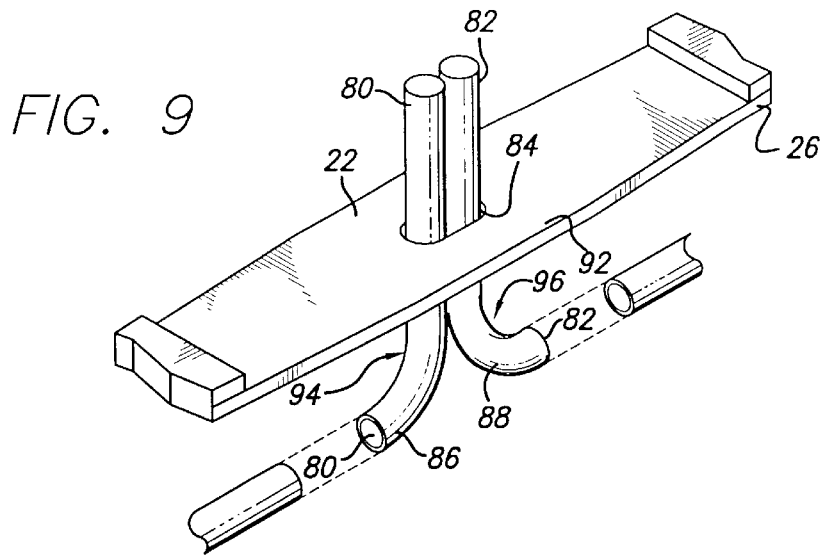
FIG. 9 is an enlarged view of the formation of a thermocouple sensor in a slot at an electrode, in accordance with an aspect of the invention.

One temperature sensor 78 found to be usable is a thermocouple. Such a sensor is shown in further detail in FIGS. 9, 10, and 11. A pair of wires 94 and 96 are brought to a slot 84 in the electrode 22. In this case, the slot 84 is of the form of an oval. The use of a longitudinally-oriented slot 84 in the electrode 22 provides the benefit of increased strength of the electrode in that there remains a substantial amount of electrode material between the slot and the lateral edge of the electrode. This strengthens the electrode and makes it less susceptible to fractures that may otherwise be caused by repeated actuation. This shape of the slot 84 also increases the attachment strength of the thermocouple to the electrode. There is less open space between the conductors of the thermocouple and the slot edges and in addition, where the solder mound 90 is hemispheric in shape, as shown in FIG. 11, there is more electrode material under the solder mound making it a stronger attachment.

The conductor portions 80 and 82 of the wires are formed of thermocouple compatible materials, such as one wire 80 formed of copper and the other 82 formed of constantan. The conductors 80 and 82 are brought together through the slot 84 and are welded together. Each wire 94 and 96 has insulation 86 and 88 and each wire is pulled through the slot 84 until its insulation is touching the bottom of the arm 26 at the slot 84. The slot 84 is made large enough for only the wires to pass but not their insulation.

The two welded wires 80 and 82 are soldered 90 in place in the slot 84. The solder forms the mound 90 on the opposite side of the slot from the insulation side. The mound 90 secures the wires to the electrode and prevents the wires 94 and 96 from becoming detached. Connecting the two wires 94 and 96 as shown and described results in the formation of a thermocouple that provides signals representative of the temperature the electrode is experiencing. In these figures, the insulation is removed 92 in the center of the arm 26 to form the electrode and for receipt of the temperature sensor. The thickness of the insulation is exaggerated in the figures for illustrative purposes only. Because the sensor 78 is small in comparison with the entire electrode surface area, it should allow for a large contact surface of the electrode to the target tissue.

Figure 10:
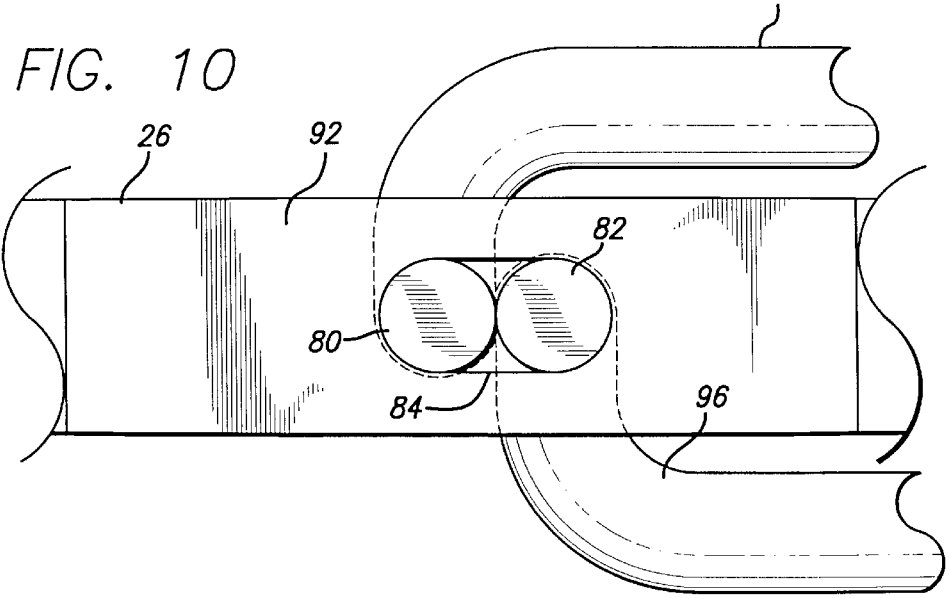
FIG. 10 is a top plan partly-fragmentary, partly-sectional enlarged view of the thermocouple of FIG. 9 showing the routing of the thermocouple wires in accordance with an aspect of the present invention.
Figure 11:
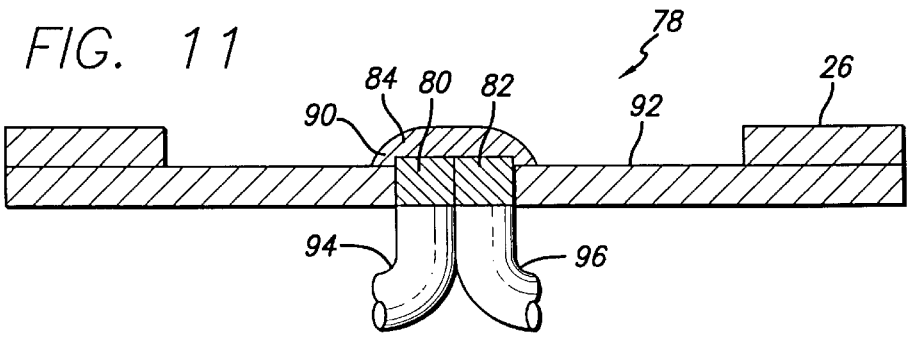
FIG. 11 is a cross-sectional enlarged view of a thermocouple temperature sensor formed in an electrode, in accordance with the present invention.

Referring now particularly to FIG. 10, as the thermocouple wires 94 and 96 leave the slot 84, they are disposed on either side of the expandable arm so as to provide equal weight on both sides of the arm and equal resistance to expansion and contraction of the arm. They are held in place on either side of each arm by the working end tip sleeve 38 (FIG. 3), as the rings 42 and 46 are. In another embodiment, a bifilar or two-conductor wire is used for the thermocouple. Although not shown, the wires proceed into the tip 30 located in relation to their respective expandable arm as shown in FIG. 10, and are bent in a 180° curve in the tip 30. They are potted in place in the tip 30 with epoxy or other material. The wires are then wound around the lumen 64 as they proceed to the connecting end of the catheter. Locating them in this manner removes them from possible interference with the slidable outer tube 52 and stop tube 54 thus making the configuration more reliable. The wires are not bonded to the outer diameter of the lumen 64.

The slot 84 for the temperature sensor may have other shapes, such as a rectangle or circle. It is preferable that the slot be longer than it is wide so that as much material exists between the slot and the lateral edge of the electrode as possible. Additionally, it is preferable that the slot is just large enough for the thermocouple wires to be inserted, but not large enough for the solder that joins the two wires to be pulled through or for the insulation surrounding the wires to be pulled through. With this configuration, the solder anchors the wires to the electrode and prevents pulling out in one direction and the insulation around the wires anchors the wires to the electrode and prevents pulling out in the other direction.

Although the insulation on the arms shown in FIGS. 3, 4, 9, and 11 appears to have a substantial depth, it is shown this way for clarity of illustration only. Those skilled in the art will recognize that the actual insulation thickness will be much less, depending on the material used.

Figure 12:
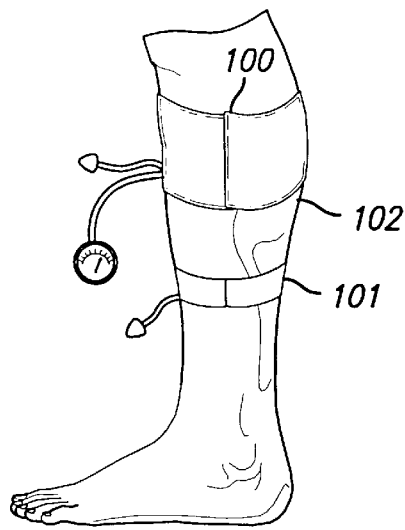
FIG. 12 is a view of the application of a pressure device to the lower limb of a patient.
Figure 13:
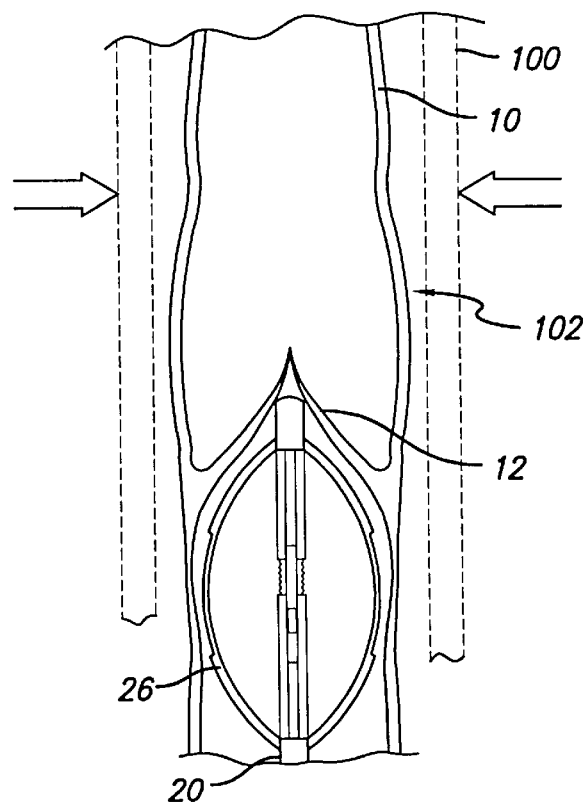
FIG. 13 is a schematic, cross-sectional view of a vein valve compressed into coaptation by the external compressive forces of the pressure device of FIG. 12 and the treatment of that valve by a catheter device.

Referring now to FIGS. 12 and 13, a pressure application device 100 can be applied externally to the area of the treatment site 102 and is adjusted to exert pressure thereon sufficient to compress the underlying vein to substantially the desired reduced diameter. The catheter 20 is advanced to that treatment site and needs to expand much less due to the external pressure that has already compressed the vein. This allows for use of smaller catheters with less expansion of the arms. The reduction in diameter by the pressure application device prior to the application of energy pre-sets the vein to the final, desired diameter. This eliminates the need to reduce the diameter of the electrodes during the treatment to bring the vein down to the final diameter. After terminating the energy application to shrink the vein wall to the size at which the external pressure application device is holding it, the pressure application device 100 can be released. The pressure application device 100 may comprise for example the manually inflated tourniquet as shown.

Where the catheter includes a guide wire lumen and/or a fluid delivery lumen, fluid may be introduced to the blood stream during RF heating of the vein being treated. This delivered fluid may be at a cooler temperature, such as room temperature, than the venous tissue being heated and may transiently lower the surface temperature of that tissue. As shown above, the temperature sensors 78 contact the surface of the venous tissue and may sense this transient temperature reduction. The fluid may also be delivered through ports formed along the side of the catheter near the working end and the electrodes (not shown). The fluid may also be delivered through a sheath which is coaxial with the catheter. In previous systems, the decrease in temperature could result in the increased application of energy by the electrodes 22 to the venous tissue. However, this is an undesirable result as the temperature decrease is only transitory and such an increase in energy applied to the venous tissue may cause an overshoot in the application of energy.

Figure 14:
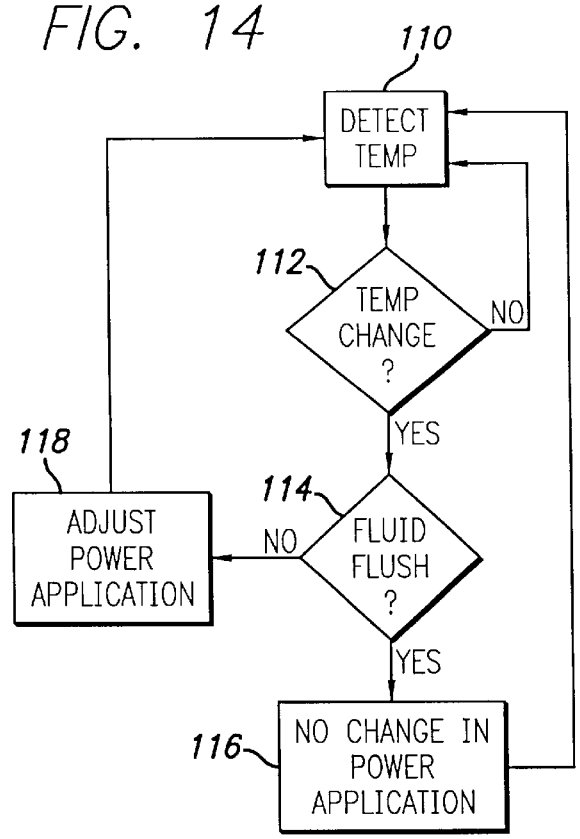
FIG. 14 is a flow chart illustrating the operation of the system of FIG. 2 in response to the introduction of a fluid flush.

In accordance with the system of the invention, should the microprocessor 76 detect a transitory temperature decrease, it will maintain the applied power level the same as before the temperature reduction and will not permit an increase in applied power. Referring now to FIG. 14, and secondarily to FIGS. 2 and 3, the temperature sensors 78 and microprocessor 76 detect the temperature 110. The microprocessor 76 determines if a temperature change 112 is occurring. If no temperature change is occurring, the sensors 78 and the microprocessor 76 continue to detect the temperature 110. However, if a temperature change is occurring, the microprocessor 76 checks for the occurrence of a fluid flush 114. In particular, the combined magnitude and duration of the temperature change are monitored. If the microprocessor 76 detects a rapid temperature change (dT/dt) of a short duration but with a large magnitude, the microprocessor 76 determines that a fluid flush is occurring and holds the application of power to the electrodes 22 at the present level 116. For example, if the temperature decreases 10° C. for a period of 2 to 3 seconds, the occurrence of a fluid flush is determined. The sensors 78 and the microprocessor 76 continue to detect the temperature 110. However, if a fluid flush is not detected 114, the microprocessor 76 is free to adjust the power level 118 through the RF generator 74. Such a case may occur where the temperature decreases 10° C. and remains at that level for 20 seconds. Through the above system, a "blanking" period is provided during which the application of power is maintained at a constant level.

At the initiation of power application to the venous tissue, an optimal rate of rise is selected. The RF generator 74 is controlled to force an exponentially increasing temperature change with a time constant of approximately ten seconds. This initial rate of change is of course ignored by the fluid flush system.

Fluids that may cause such an overshoot include a dye contrast flush for fluoroscopic visualization during treatment. Such a fluid is often used to precisely locate the position of a device in an anatomical structure.

The method of the present invention for the minimally invasive treatment of venous insufficiency preferably uses the application of RF power to the venous tissue by RF electrodes on a delivery catheter to restore the competency of a vein valve. The electrodes for generating the heating effect for shrinking the collagen in the surrounding venous tissue can be introduced either antegrade or retrograde. Particular discussion will be made of the treatment of varicose veins in the legs, though the method is well suited to treating veins in other areas of the body or for treating other biological structures in the body.

When treating the veins of the lower limbs, the patient is typically placed onto a procedure table with the feet dependent in order to fill the veins of the leg. The leg of the patient is prepped with antiseptic solution. A percutaneous introducer is inserted into the vein using a common Seldinger technique to access either the superficial or deep vein systems. Alternatively, a venous cut-down can be used to access the vein system to be treated. The procedure for the repair of incompetent veins can be accomplished by a qualified physician with or without fluoroscopic or ultrasonic observation, or under direct visualization. Further, the physician could palpate the treatment area to determine the location of the catheter, and the treatment site, during the procedure when treating the superficial venous system.

Figure 1:
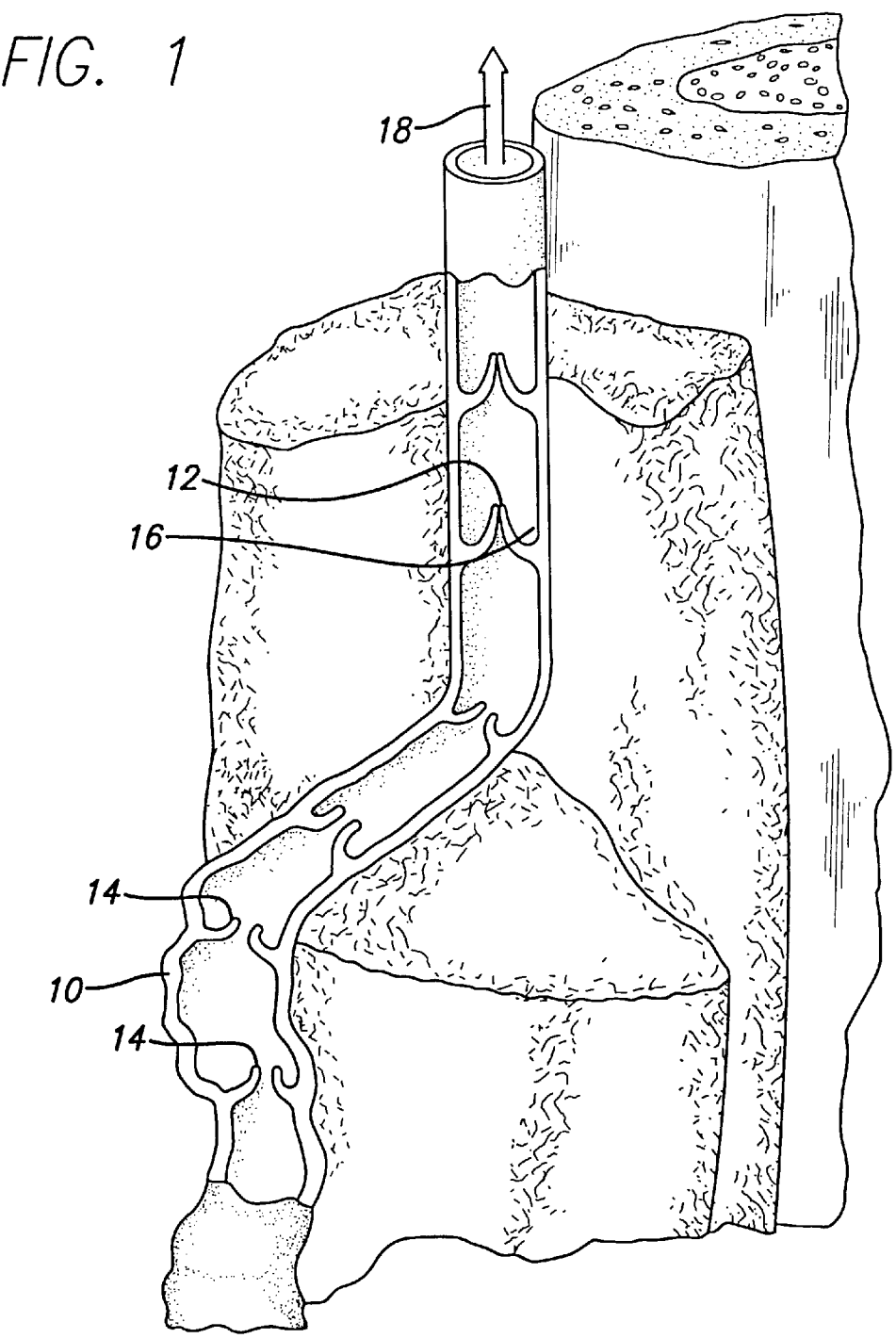
FIG. 1 is a cross-section view of a portion of a vein in a lower limb showing a segment of the vein having dilation with multiple incompetent valves which are to be treated in accordance with the present invention and a segment of the vein having fully competent valves.
Figure 15:
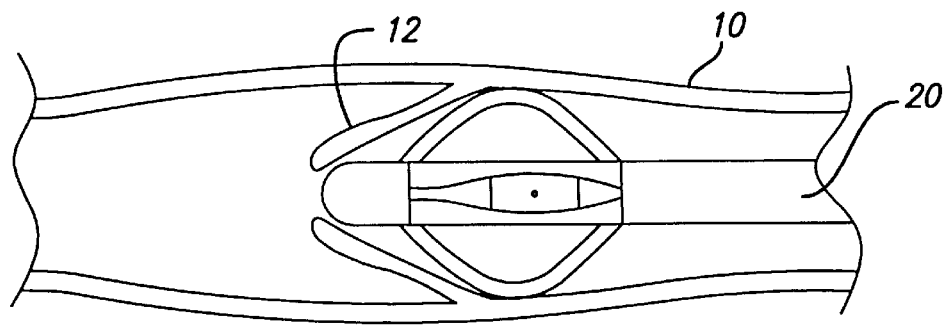
FIG. 15 is a partial cross-sectional view of the use of a catheter to treat an incompetent venous valve.

Referring to FIG. 15 and also to FIGS. 1, 2 and 3, the catheter 20 may be passed within the vein 10 after insertion through the skin. Alternatively, a guide wire 68 for the catheter 20 may be inserted into the vein. The guide wire 68 is advanced antegrade to the level of the most proximal incompetent vein valve which is to be repaired. The catheter 20 is then advanced over the guide wire 68 up the leg through the vein to the level of the dilated venous section to be treated. Fluoroscopy, ultrasound, or an angioscopic imaging technique is then used to direct the specific placement of the catheter 20 and confirm the position within the vein 10. With fluoroscopy, contrast material can be injected through or around the catheter to identify the incompetent venous sections to be repaired. A retrograde venogram can be performed in some cases to better localize the treatment site and effect.

From an antegrade approach, the catheter 20 is introduced such that the electrodes are distal to the valve 12 annulus as shown in FIG. 15. As indicated by the arrows in FIG. 13, external pressure by the tourniquet 10 (FIG. 12) has reduced the vein diameter to the diameter at which reflux is abolished. The electrodes 22 are expanded to come into apposition with the vein wall. RF energy is applied by the electrodes in order to heat the vein wall, cause collagen contraction, and durably mold the vein diameter to the reduced diameter produced by the compressive force of the external tourniquet. An RF generator (not shown) is activated to provide suitable RF energy to the electrodes, preferably at a low power level, and preferably at a selected frequency from a range of 250 kHz to 350 MHz. For example, suitable frequencies include 450 kHz and 510 kHz.

One criterion for the selection of the applied frequency is to manage electrical losses in the leads supplying power to the electrodes. Another criterion is compatibility with filter circuits which can be used to eliminate RF noise from thermocouple signals.

The properties of the treatment site, such as temperature or impedance, may be monitored to provide feedback control for the RF energy. Monitoring such values in an automatic feedback control system for the RF energy may also be used to control the heating effect and avoid overheating of the vein.

The energy emitted from the electrodes is converted within the venous tissue into heat. As the temperature of the venous tissue increases, the venous tissue can begin to durably assume the reduced diameter, due in part to the structural transfiguration of the collagen fibers in the vein. Although the collagen becomes compacted during this process, the vessel with collagen still retains elasticity. The vein would shrink further but for the mechanically bowed out electrodes defining the effective diameter of the catheter. Other schemes, such as a balloon or a helical member which can be coiled and uncoiled, may be used to mechanically limit or control the amount of shrinkage in the vein or to displace blood from the treatment site. Such mechanical schemes assure apposition between the electrodes and the venous tissue during treatment, and prevent further shrinkage so that the vein remains patent.

Energy is delivered for a predetermined time. After the application of energy is ceased, the electrodes are retracted and the catheter is pulled back from the treatment site. Vein diameter and the existence of reflux are reassessed by ultrasound through a window in the tourniquet with the electrodes retracted and the tourniquet deflated. Energy may be again applied if reflux is detected, otherwise, the treatment area can be infused with heparin or another medicant. Other venous sites can then be treated 86.

The catheter 20 includes expandable arms 26 but can include cables, an inflating balloon, or other means that can selectively move the bowable arms in order to properly position the working end of the catheter against venous tissue.

When RF energy is applied to the venous tissue at or near the incompetent valve of the dilated vein, the shrinkage of the venous tissue at or near the commissures can restore valvular competency by reducing the venous lumen dilation which is preventing the proper functioning of the venous valve. Gross shrinkage of the vein diameter or shrinkage of the venous tissue at or near the commissures can restore competency to the venous valve, by bringing the cusps and valve leaflets closer together.

The application of RF energy is terminated after there has been sufficient shrinkage of the vein to alleviate the dilation of the vein near the valve, so as to restore venous function or valvular competency. Sufficient shrinkage can be detected by fluoroscopy, external ultrasound scanning, intravascular ultrasound scanning, direct visualization using an angioscope, or any other suitable method. For example, the catheter 20 can be configured to deliver an x-ray contrast medium to allow visualization by fluoroscopy for assessing the condition of the vein and the relationship of the catheter to the treatment area of the vein during the shrinkage process. As an alternative to fluoroscopy, external ultrasound techniques such as B-scanning using distinct ultrasound signals from different angles, or intravascular ultrasound can be used to acquire a more multidimensional view of the vein shrinkage at the treatment site. An angioscope can also be used to directly visualize and determine the extent and degree of vein shrinkage.

A suitable tourniquet having an ultrasound transparent window is described in the application for U.S. patent filed by Zikorus et al. on Jun. 2, 1997, entitled Pressure Tourniquet with Ultrasound Window and Method of Use and incorporated herein by reference.

Substantial shrinkage may occur very rapidly, depending upon the specific treatment conditions. Because the shrinkage can proceed at a rather rapid rate, the RF energy is preferably applied at low power levels. As previously discussed, the frequency of the RF energy is selected to control the spread of the heating effect at the treatment site.

In an example of a process employing an external pressure application device 100 shown in FIGS. 12 and 13, an anti-coagulation dosage of Heparin is administered into the treatment site by dripping through a sheath. A catheter 20 is then introduced at the site through the sheath, and venous blood flow is stopped by the application of a tourniquet 101 applied at a position distal to the treatment site 102. The external pressure application device 100 is then pressurized to reduce the vein surrounding the treatment site 102 to the desired final diameter. The catheter arms 26 are then expanded so as to offer maximum vein wall apposition, and the test mode of the RF generator 74 is engaged to take pretreatment measurement of the vein wall impedance. Since the impedance of the vein wall is higher than that of the blood, the RF energy is optimally transferred to the vein wall with minimal RF current shunting through the blood. The insulated arms disclosed herein greatly assist in avoiding such shunting. The insulation of the arms is only removed on the outer surface of the arms to form the electrodes and remains on the inner surface and side edges which are exposed to the blood. Additionally, the arms are strong enough to prevent shrinkage of the vein beyond the diameter set by the arms. RF energy application is actuated and controlled in reference to temperature and power treatment parameters. Optimal control of the maximum temperature is afforded in the temperature control mode of the RF generator 74 and microprocessor 76 which employ a PID control algorithm so that RF power is adjusted to maintain a constant set temperature. At the time when the set temperature is reached, the arms 26 are maintained at full apposition with the vein wall for a selected time period to shrink the wall to the desired diameter set by the external pressure device 100. The rigidity of the arms prevent shrinkage of the vein wall further.

In another approach, electrode diameter reduction is accomplished in multiple steps. In this approach, the external pressure device 100 is applied to reduce the vein diameter in multiple steps to finally reach the desired reduced diameter. At each step, the electrodes are actuated to shrink the venous lumen to that step size in the manner described above.

In yet another approach, the vein wall is shrunk in a continuous manner to reach the final desired diameter. In this approach, the electrodes are placed in apposition with the vein wall, energy is applied to the vein wall by the electrodes, and the electrodes are slowly retracted as the vein wall shrinks while maintaining continuous contact with the vein wall during shrinkage. At the desired final diameter of the vein wall, the electrodes restrain the vein wall from further shrinkage. In this approach, the external pressure device 100 need not be used.

After treating the first venous section shown, the catheter 20 can be moved to the next venous valve suffering from insufficiency. The catheter 20 can be repositioned to treat as many venous sections and valves as necessary. RF energy is applied to each venous section to be repaired, until all of the desired venous sections are repaired and the valves are rendered competent. Multiple incompetent valves and dilated venous sections can be treated and repaired in a single minimally invasive procedure. If desired, a second introducer can be inserted into the limb of a patient in order to access either the deep or the superficial vein system, whichever has yet to be treated. The catheter can then be used to treat incompetent venous sections in the other vein system.

After completing the RF procedure for each selected venous section, the catheter and electrodes are removed from the vasculature. The access point of the vein would be sutured closed if a cutdown had been performed, or local pressure would be applied after percutaneous sheath removal until bleeding was controlled. A bandage would then be applied. A pressure dressing may be necessary.

As an alternative to the antegrade approach, the catheter 20 can deliver its electrodes 22 to the venous treatment site from a retrograde approach. The catheter 20 would be introduced into a percutaneous sheath that has been inserted through the skin and into the vein in a retrograde direction.

As can be readily ascertained from the disclosure herein, the surgical procedure of the present invention is accomplished without the need for prolonged hospitalization or post-operative recovery. The restoration of venous function is possible without the need for continued lifestyle changes, such as frequent leg elevation, the wearing of elastic support stockings, or prolonged treatment of recurrent venous stasis ulcers. Moreover, the need for surgery of the valves themselves (valvuloplasty) or surgery of the arm and leg for transplantation of arm veins into the leg would not be necessary.

Early treatment of venous disease could prevent more serious complications such as ulceration, and valve damage caused by thrombophlebitis or thromboembolism. The cost of treatment and complications due to venous disease would be significantly reduced. There would be no need for extensive hospitalization for this procedure, and the need for subsequent treatment and hospitalization would also be reduced from what is currently needed. Furthermore, the minimally invasive nature of the disclosed methods would allow the medical practitioner to repair or treat several vein sections in a single procedure in a relatively short period of time with minimal recuperation time.

It is to be understood that the type and dimensions of the catheter and electrodes may be selected according to the size of the vein to be treated. Although the present invention has been described as treating venous insufficiency of the lower limb such as varicose veins in the leg, the present invention can be used to intraluminally treat venous insufficiency in other areas of the body. For example, hemorrhoids may be characterized as outpocketed varicose veins in the anal region. Traditional treatments include invasive surgery, elastic ring ligation, and the application of topical ointments. Shrinking the dilated veins using RF energy can be accomplished in accordance with the present invention. Specifically, the catheter and electrode combination is introduced into the venous system, into the external iliac vein, the internal iliac vein, then either the hemorrhoidal or the pudendal vein. The catheter then delivers the electrode to the site of the dilated hemorrhoidal vein by this transvenous approach. Fluoroscopic techniques or any other suitable technique such as pulse-echo ultrasound, as previously discussed, can be used to properly position the electrode at the venous treatment site. The treatment site is preferably selected to be at least two centimeters above the dentate line to minimize pain. The electrode applies RF energy at a suitable frequency to minimize coagulation for a sufficient amount of time to shrink, stiffen, and fixate the vein, yet maintain venous function or valvular competency. This intraluminal approach avoids the risks and morbidity associated with more invasive surgical techniques such as hemorrhoidectomy, while significantly reducing reflux of blood in the area without necrosis or removing the venous tissue.

Another area of venous insufficiency relates to erectile impotency of the penis. A significant number of all physically-induced cases of impotence result from excessive drainage of blood from the penile venous system. Venous-drainage-impotence can be treated using the present invention. Catheters having a sufficiently small diameter can be used to deliver the electrodes through the dorsal vein of the penile venous system to shrink this venous outflow path. Fluoroscopic or ultrasound techniques can be used to properly position the electrode within the incompetent vein. RF energy or other radiant energy is applied from the electrodes at a suitable frequency to shrink the surrounding venous tissue in order to reduce the excessive amount of drainage from the penis while maintaining venous function or valvular competency. The amount of shrinkage of the vein can be limited by the diameter of the catheter itself, or the catheter or electrodes themselves can be expanded to the appropriate size. Ligation of these veins should be avoided so as to allow for the proper drainage of blood from an engorged penis which is necessary for proper penile function.

Another area of venous insufficiency suitable for treatment in accordance with the present invention involves esophageal varices. Varicose veins called esophageal varices can form in the venous system along the submucosa of the lower esophagus, and bleeding can occur from the swollen veins. Properly sized catheters can be used in accordance with the present invention to deliver the electrodes to the site of venous insufficiency along the esophageal varices. Endovascular access for the catheter is preferably provided through the superior mesenteric vein or portal vein to shrink the portal vein branches leading to the lower esophagus. Proper positioning of the electrode within the vein can be confirmed using fluoroscopic or ultrasound techniques. The electrodes apply RF energy or other radiant energy at a suitable frequency to shrink the vein and reduce the swelling and transmission of high portal venous pressure to the veins surrounding the esophagus.

Although described above as positively charged, negatively charged, or as a positive conductor or negative conductor, or as having one polarity or another, these terms are used for purposes of illustration only. These terms are generally meant to refer to different potentials and are not meant to indicate that any particular voltage is positive or negative.

Although described as applying RF energy from the electrodes, it is to be understood that other forms of energy such as microwaves, ultrasound, lower frequency electrical energy, direct current, circulating heated fluid, radiant light, and LASERs may be used, and that the thermal energy generated from a resistive coil or curie point element may be used as well.

While several particular forms of the invention have been illustrated and described, it will be apparent that various modifications can be made without departing from the spirit and scope of the invention. Accordingly, it is not intended that the invention be limited, except as by the appended claims.

What is claimed is:

1. A method of applying energy to a hollow anatomical structure, comprising:

introducing a delivery device having an energy application device into a hollow anatomical structure containing collagen;

positioning the energy application device at a treatment site in the hollow anatomical structure;

molding the hollow anatomical structure to a specific size using external compression;

applying energy from the energy application device to alter the collagen in the hollow anatomical structure such that the hollow anatomical structure will remain at the specific size without external compression.

2. The method of applying energy of claim 1, further comprising:

expanding the energy application device into contact with the hollow anatomical structure, after positioning the energy application device at the treatment site.

3. The method of applying energy of claim 2, wherein the energy application device in the step of expanding comprises a plurality of expandable electrodes.

4. The method of applying energy of claim 1, wherein the step of applying energy includes the step of applying RF energy, wherein the energy application device includes a plurality of electrodes.

5. The method of applying energy of claim 1, wherein the step of applying energy includes the step of applying laser energy, wherein the energy application device includes a laser.

6. The method of applying energy of claim 1, wherein the hollow anatomical structure is a vein.

7. The method of applying energy of claim 1, wherein the hollow anatomical structure is a tubular conduit.

8. The method of applying energy of claim 1, wherein the collagen becomes compacted during the step of applying energy from the energy application device to the hollow anatomical structure to alter the collagen in the hollow anatomical structure, and the collagen retains elasticity after the step of applying energy.

* * * * *